(12) United States Patent
Busch et al.

(10) Patent No.: US 9,212,120 B2
(45) Date of Patent: Dec. 15, 2015

(54) PROCESS FOR PREPARING SPIRO[2.5]OCTANE-5,7-DIONE

(71) Applicants: Torsten Busch, Frankfurt am Main (DE); Sven Anklam, Kelkheim (DE); Joerg Jung, Floersheim (DE); Markus Ostermeier, Biberach an der Riss (DE)

(72) Inventors: Torsten Busch, Frankfurt am Main (DE); Sven Anklam, Kelkheim (DE); Joerg Jung, Floersheim (DE); Markus Ostermeier, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/445,371

(22) Filed: Jul. 29, 2014

(65) Prior Publication Data

US 2014/0336405 A1 Nov. 13, 2014

Related U.S. Application Data

(62) Division of application No. 13/956,604, filed on Aug. 1, 2013, now abandoned.

(30) Foreign Application Priority Data

Aug. 3, 2012 (EP) ..................................... 12005681
Oct. 2, 2012 (EP) ..................................... 12186998

(51) Int. Cl.

| | | |
|---|---|---|
| *C07D 311/96* | (2006.01) | |
| *C07C 45/65* | (2006.01) | |
| *C07C 67/08* | (2006.01) | |
| *C07C 67/30* | (2006.01) | |
| *C07C 67/343* | (2006.01) | |
| *C07C 259/06* | (2006.01) | |
| *C07C 69/608* | (2006.01) | |
| *C07C 69/716* | (2006.01) | |
| *C07C 45/45* | (2006.01) | |
| *C07C 51/08* | (2006.01) | |
| *C07C 51/083* | (2006.01) | |
| *C07C 49/443* | (2006.01) | |
| *C07C 59/205* | (2006.01) | |
| *C07C 69/635* | (2006.01) | |

(52) U.S. Cl.
CPC ............... *C07C 45/65* (2013.01); *C07C 45/455* (2013.01); *C07C 49/443* (2013.01); *C07C 51/08* (2013.01); *C07C 51/083* (2013.01); *C07C 59/205* (2013.01); *C07C 67/08* (2013.01); *C07C 67/30* (2013.01); *C07C 67/343* (2013.01); *C07C 69/608* (2013.01); *C07C 69/635* (2013.01); *C07C 69/716* (2013.01); *C07C 259/06* (2013.01); *C07D 311/96* (2013.01); *C07C 2101/02* (2013.01); *C07C 2102/50* (2013.01)

(58) Field of Classification Search
CPC ....................................................... C07D 311/96
USPC .................................................. 549/330, 331
See application file for complete search history.

(56) References Cited

U.S. PATENT DOCUMENTS

| 5,021,443 A | 6/1991 | Bru-Magniez et al. |
| 5,124,336 A | 6/1992 | Bru-Magniez et al. |
| 2008/0194609 A1 | 8/2008 | Bischoff et al. |

FOREIGN PATENT DOCUMENTS

| CA | 2591486 A1 | 7/2006 |
| WO | 2006072362 A1 | 7/2006 |
| WO | 2010127452 A1 | 11/2010 |

OTHER PUBLICATIONS

International Search Report for PCT/EP2013/066031 mailed on Oct. 23, 2013.
Powell, et al. "Indoles and related compounds as OXE receptor antagonists and their preparation and use for the treatment of diseases" Accession No. 2010:1400882. STN International HCAPLUS database.
Qudrat-I-Kuda, Muhammad "CI—Studies in Keto-Iactol Tautomerism. Part II. Influence of the cycloHexane Ring on the Tautomeric Character of cycloHexane-1-acetone-1-malonic Acid, a Comparison with cycloPentane-1-acetone-1-malonic Acid, and Synthesis of the Corresponding d-Keto-monobasic Acids" Published Jan. 1929. Imperial College of Science and Technology, 9 pgs.

*Primary Examiner* — Golam M M Shameem
(74) *Attorney, Agent, or Firm* — Michael P. Morris; Usha R. Patel

(57) ABSTRACT

Disclosed is a method for the synthesis of spiro[2.5]octane-5,7-dione useful as intermediate in the manufacture of pharmaceutically active ingredients. Also disclosed are novel intermediates used in the synthesis of this compound.

3 Claims, No Drawings

PROCESS FOR PREPARING SPIRO[2.5]OCTANE-5,7-DIONE

TECHNICAL FIELD

This invention relates to a novel process or method for the synthesis of spiro[2.5]octane-5,7-dione useful as intermediate in the manufacture of pharmaceutically active ingredients.

BACKGROUND

Spiro[2.5]octane-5,7-dione is an important intermediate for the production of pharmaceutically active ingredients. The synthesis of this intermediate has been described in WO 2006/72362 and is quite complex, costly and unattractive for larger quantities. Therefore there is a need for a new synthesis route to manufacture spiro[2.5]octane-5,7-dione efficiently and in the high quality needed for pharmaceutical intermediates.

DESCRIPTION OF THE INVENTION

The present invention provides an efficient process for the manufacture of spiro[2.5]octane-5,7-dione having the formula

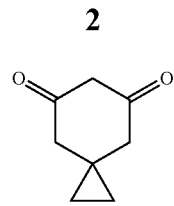

in the steps as described herein below.

A general process for preparing spiro[2.5]octane-5,7-dione is outlined in Scheme 1. In one embodiment, the present invention is directed to the general multi-step synthetic method for preparing spiro[2.5]octane-5,7-dione as set forth in Scheme 1 below. In other embodiments, the invention is directed to each of the individual steps of Scheme 1 and any combination of two or more successive steps of Scheme 1. The invention may also be directed to the intermediate compounds, e.g. as set forth in Scheme 1.

Scheme 1. Process for the manufacture of spiro[2.5]octane-5,7-dione according to the invention (aspect 1 of the invention):

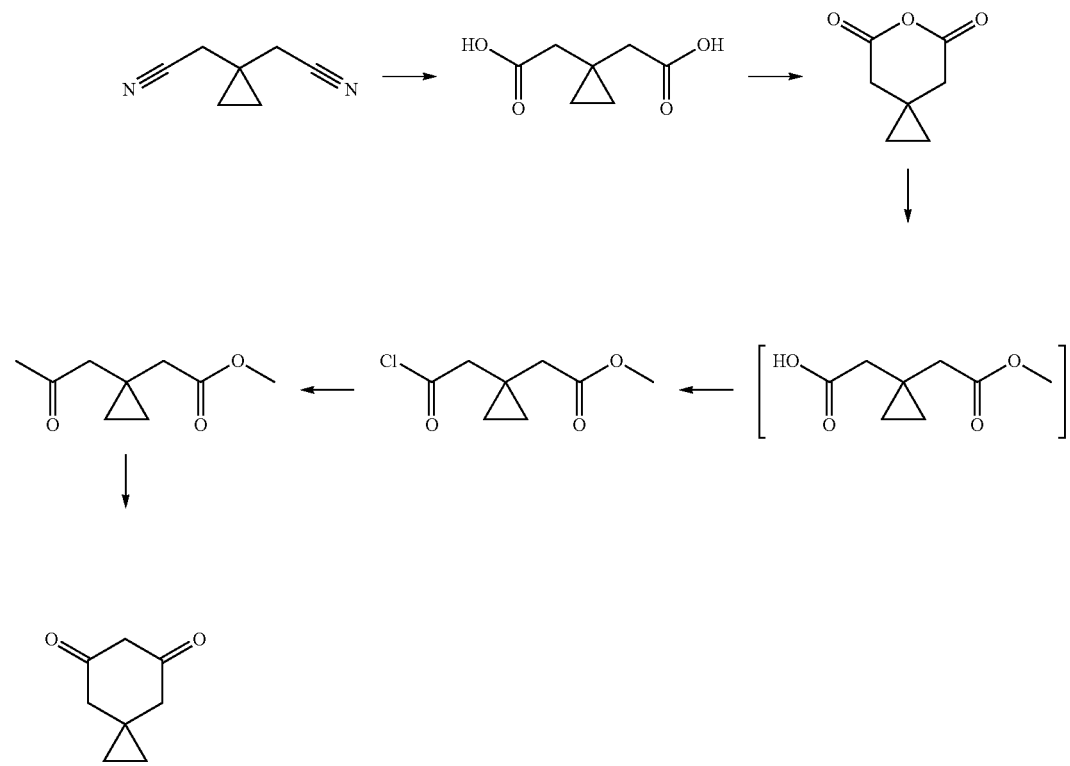

An alternative general process for preparing spiro[2.5]octane-5,7-dione is outlined in Scheme 2. In one embodiment, the present invention is directed to the general multi-step synthetic method for preparing spiro[2.5]octane-5,7-dione as set forth in Scheme 2 below. In other embodiments, the invention is directed to each of the individual steps of Scheme 2 and any combination of two or more successive steps of Scheme 2. The invention may also be directed to the intermediate compounds, e.g. as set forth in Scheme 2.

Scheme 2. Alternative process for the manufacture of spiro[2.5]octane-5,7-dione according to the invention (aspect 2 of the invention):

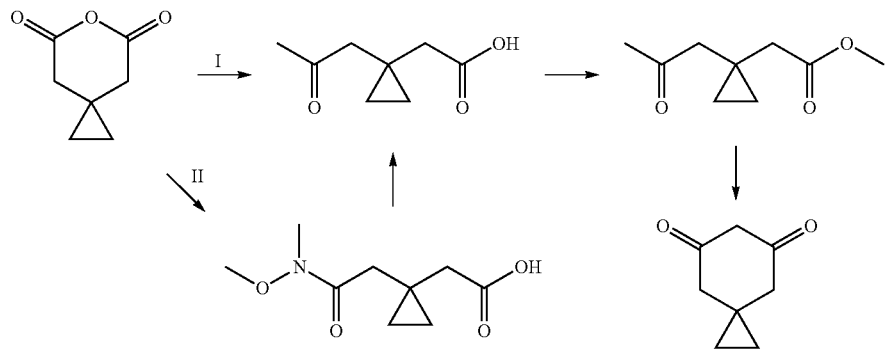

Thus, in one aspect, the present invention relates to a process for the manufacture of spiro[2.5]octane-5,7-dione having the formula

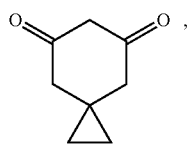

said process comprising the following steps (Scheme 1):

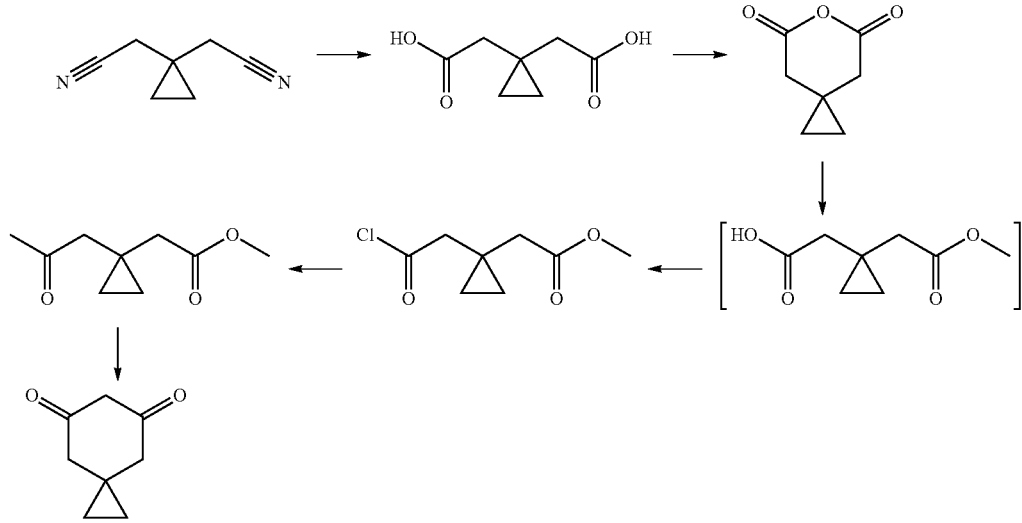

Accordingly, the present invention further relates to one or more of the above steps of Scheme 1.

With reference to the steps shown in Scheme 1 of the invention, a process or method according to the present invention comprises one or more of the following:
  hydrolizing (1-cyanomethyl-cyclopropyl)-acetonitrile to form (1-carboxymethyl-cyclopropyl)-acetic acid (such as e.g. in the presence of a suitable base, such as aqueous potassium hydroxide),
  cyclizing (1-carboxymethyl-cyclopropyl)-acetic acid to form 6-oxa-spiro[2.5l]octane-5,7-dione (such as e.g. in the presence of a suitable carboxylic acid anhydride forming agent, such as acetanhydride, preferably in mesitylene as reaction solvent, at elevated temperature),
  reacting 6-oxa-spiro[2.5]octane-5,7-dione with an alcohol (e.g. $C_1$-$C_6$ alkanol, preferably $C_1$-$C_4$ alkanol, more preferably $C_1$-$C_3$ alkanol or even more preferably $C_1$-$C_2$ alkanol, particularly methanol) to form (1-alkoxycarbonylmethyl-cyclopropyl)-acetic acid (such as e.g. in the presence of 4-dimethylaminopyridine as promotor, preferably in a reaction medium comprising an excess of the alcohol and/or toluene, at elevated temperature),
  converting (1-alkoxycarbonylmethyl-cyclopropyl)-acetic acid into the corresponding (1-alkoxycarbonylmethyl-cyclopropyl)-acetic acid chloride (such as e.g. in the presence of a suitable carboxylic acid chloride forming agent, such as thionyl chloride, preferably in the presence of N,N-dimethylformamide as promotor, preferably in toluene as reaction medium),
  methylation of (1-alkoxycarbonylmethyl-cyclopropyl)-acetic acid chloride to form [1-(2-oxo-propyl)-cyclopropyl]-acetic acid alkyl ester (such as e.g. in the presence of a suitable nucleophilic methylating agent, such as e.g. a methyl magnesium (Grignard) in the presence of an iron containing catalyst, or a methyl copper reagent, preferably in a reaction solvent comprising toluene and/or tetrahydrofurane), cyclizing [1-(2-oxo-propyl)-cyclopropyl]-acetic acid alkyl ester to form spiro[2.5]octane-5,7-dione (such as e.g. in the presence of a suitable base, such as a respective metal alcoholate (e.g. sodium methanolate, sodium ethanolate, or the like), preferably in a reaction solvent comprising tetrahydrofurane and/or the respective alcohol).

Further thus, in another aspect, the present invention relates to a process for the manufacture of spiro[2.5]octane-5,7-dione having the formula

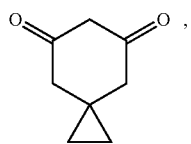

said process comprising the following steps (Scheme 2), either via variant I or via variant II:

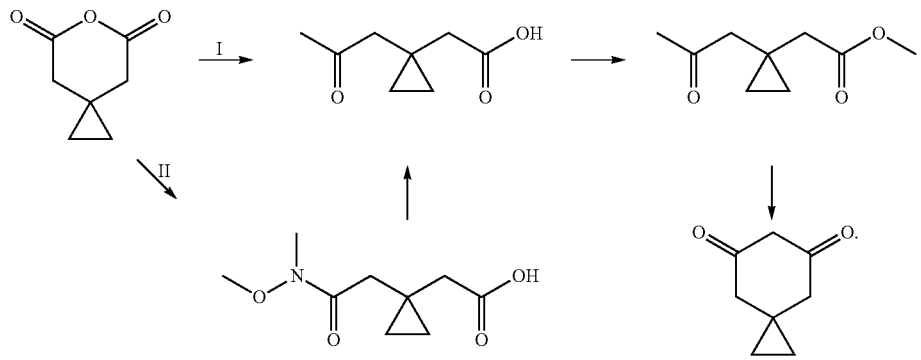

Accordingly, the present invention further relates to one or more of the above steps of Scheme 2.

With reference to the steps shown in variant I of Scheme 2 of the invention, a process or method according to the present invention comprises one or more of the following:

ring opening methylation of 6-oxa-spiro[2.5]octane-5,7-dione to form [1-(2-oxo-propyl)-cyclopropyl]-acetic acid (such as e.g. in the presence of a suitable nucleophilic methylating agent, such as e.g. a methyl copper reagent, or a methyl magnesium (Grignard) reagent in the presence of a metal (e.g. Fe or Cu) containing catalyst, preferably in a reaction solvent comprising tetrahydrofurane), esterification of [1-(2-oxo-propyl)-cyclopropyl]-acetic acid with an alcohol (e.g. $C_1$-$C_6$ alkanol, preferably $C_1$-$C_4$ alkanol, more preferably $C_1$-$C_3$ alkanol or even more preferably $C_1$-$C_2$ alkanol, particularly methanol) to form [1-(2-oxo-propyl)-cyclopropyl]-acetic acid alkyl ester (such as e.g. in the presence of a suitable acid (e.g. hydrochloric acid), preferably in a suitable reaction solvent comprising an excess of the alcohol and/or mesitylene, at elevated temperature), cyclizing [1-(2-oxo-propyl)-cyclopropyl]-acetic acid alkyl ester to form spiro[2.5]octane-5,7-dione (such as e.g. in the presence of a suitable base, such as a respective metal alcoholate (e.g. sodium methanolate, sodium ethanolate, or the like), preferably in a reaction solvent comprising tetrahydrofurane and/or the respective alcohol).

With reference to the steps shown in variant II of Scheme 2 of the invention, a process or method according to the present invention comprises one or more of the following:

reacting 6-oxa-spiro[2.5]octane-5,7-dione with N,O-dimethylhydroxylamine to form {1-[(methoxy-methyl-carbamoyl)-methyl]-cyclopropyl}-acetic acid (such as e.g. in the presence of a suitable base (e.g. pyridine)), methylation of {1-[(methoxy-methyl-carbamoyl)-methyl]-cyclopropyl}-acetic acid to form [1-(2-oxo-propyl)-cyclopropyl]-acetic acid (such as e.g. in the presence of a suitable nucleophilic methylating agent, such as methyl lithium, methyl copper or methyl magnesium (Grignard) reagent, optionally in the presence of a metal (e.g. Fe or Cu) containing catalyst, preferably in a reaction solvent comprising tetrahydrofurane), esterification of [1-(2-oxo-propyl)-cyclopropyl]-acetic acid with an alcohol (e.g. $C_1$-$C_6$ alkanol, preferably $C_1$-$C_4$ alkanol, more preferably $C_1$-$C_3$ alkanol or even more preferably $C_1$-$C_2$ alkanol, particularly methanol) to form [1-(2-oxo-propyl)-cyclopropyl]-acetic acid alkyl ester (such as e.g. according to above-described conditions), cyclizing [1-(2-oxo-propyl)-cyclopropyl]-acetic acid alkyl ester to form spiro[2.5]octane-5,7-dione (such as e.g. according to above-described conditions).

In certain more detailed embodiments of the invention, the present invention relates to the process and/or the individual process steps substantially as described by way of example in the following examples.

Further, the invention relates to a compound useful as intermediate selected from:

(1-Carboxymethyl-cyclopropyl)-acetic acid,

6-Oxa-spiro[2.5]octane-5,7-dione, (1-Methoxycarbonylmethyl-cyclopropyl)-acetic acid, (1-Chlorocarbonylmethyl-cyclopropyl)-acetic acid methyl ester,

[1-(2-Oxo-propyl)-cyclopropyl]-acetic acid methyl ester,

[1-(2-Oxo-propyl)-cyclopropyl]-acetic acid, and

{1-[(Methoxy-methyl-carbamoyl)-methyl]-cyclopropyl}-acetic acid, or a tautomer or salt thereof.

In a further embodiment, the present invention is not limited to the use of a methyl ester of formula

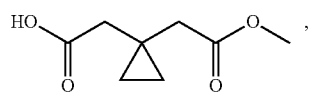

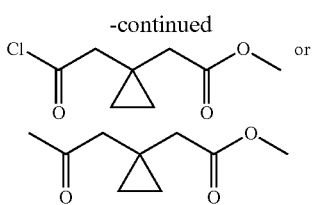

within the processes or methods according to the present invention, in addition to the respective methyl esters, a broader genus of esters of formula

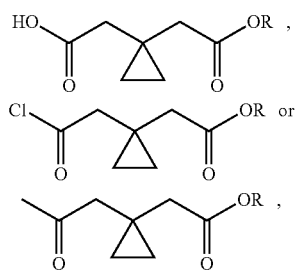

in each of which R may be $C_1$-$C_6$ alkyl, preferably $C_1$-$C_4$ alkyl (such as e.g. methyl, ethyl, propyl, isopropyl, or the like), more preferably $C_1$-$C_3$ alkyl or even more preferably $C_1$-$C_2$ alkyl, particularly methyl, may be considered.

Accordingly, in alternative embodiments, the present invention refers to processes or methods as disclosed hereinabove or hereinbelow (e.g. Scheme 1 or Scheme 2) wherein a compound of formula

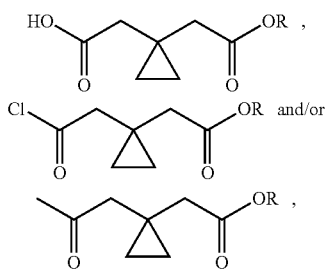

in each of which R is $C_1$-$C_6$ alkyl, preferably $C_1$-$C_4$ alkyl (such as e.g. methyl, ethyl, propyl, isopropyl, or the like), more preferably $C_1$-$C_3$ alkyl or even more preferably $C_1$-$C_2$ alkyl, particularly methyl, is used or involved instead of a compound of formula

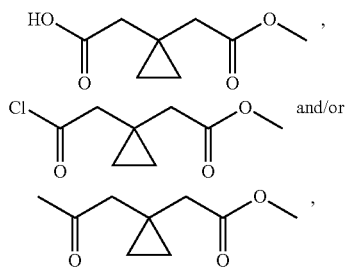

respectively.

In a particular embodiment, the present invention provides and relates to the following compound or a salt thereof as well as its preparation:

6-Oxa-spiro[2.5]octane-5,7-dione having the formula:

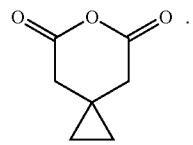

In a particular embodiment, the present invention provides and relates to the following compound or a salt thereof, as well as its preparation:

(1-Methoxycarbonylmethyl-cyclopropyl)-acetic acid having the formula:

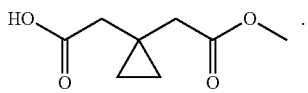

In a particular embodiment, the present invention provides and relates to the following compound or a salt thereof, as well as its preparation:

(1-Chlorocarbonylmethyl-cyclopropyl)-acetic acid methyl ester having the formula:

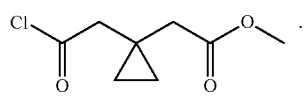

In a particular embodiment, the present invention provides and relates to the following compound or a salt thereof, as well as its preparation:

[1-(2-Oxo-propyl)-cyclopropyl]-acetic acid methyl ester having the formula:

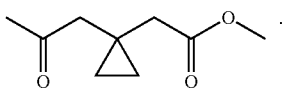

In another embodiment, the present invention provides and relates to the following compound or a salt thereof, as well as its preparation:

[1-(2-Oxo-propyl)-cyclopropyl]-acetic acid having the formula:

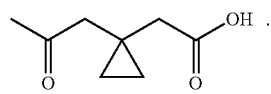

In another embodiment, the present invention provides and relates to the following compound or a salt thereof, as well as its preparation:

{1-[(Methoxy-methyl-carbamoyl)-methyl]-cyclopropyl}-acetic acid having the formula:

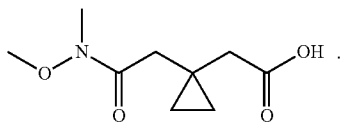

In a further embodiment, the present invention provides and relates to the following compound or a salt thereof, as well as its preparation:

wherein R is $C_1$-$C_6$ alkyl, preferably $C_1$-$C_4$ alkyl (such as e.g. methyl, ethyl, propyl, isopropyl, or the like), which may be prepared analogously to the methyl ester as described herein and may be also useful as intermediates within the present invention.

In a further embodiment, the present invention provides and relates to the following compound or a salt thereof, as well as its preparation:

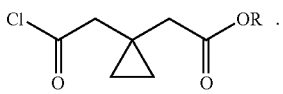

wherein R is preferably $C_1$-$C_6$ alkyl, preferably $C_1$-$C_4$ alkyl (such as e.g. methyl, ethyl, propyl, isopropyl, or the like), which may be prepared analogously to the methyl ester as described herein and may be also useful as intermediates within the present invention.

In a further embodiment, the present invention provides and relates to the following compound or a salt thereof, as well as its preparation:

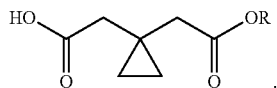

wherein R is $C_1$-$C_6$ alkyl, preferably $C_1$-$C_4$ alkyl (such as e.g. methyl, ethyl, propyl, isopropyl, or the like), which may be prepared analogously to the methyl ester as described herein and may be also useful as intermediates within the present invention.

In certain embodiments, the present invention relates to an indicated intermediate in isolated form, such as e.g. in solid or crystalline form.

In certain embodiments, the present invention relates to an indicated intermediate in solution form.

Further, the present invention relates to spiro[2.5]octane-5,7-dione obtainable or obtained by a process or method according to the present invention.

Further, the present invention relates in particular to spiro[2.5]octane-5,7-dione having the formula

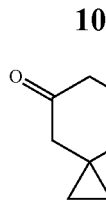

obtainable or obtained by cyclization of [1-(2-oxo-propyl)-cyclopropyl]-acetic acid methyl ester having the formula

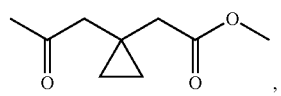

such as e.g. substantially as described herein.

Further, the present invention relates in particular to a method of preparing spiro[2.5]octane-5,7-dione having the formula

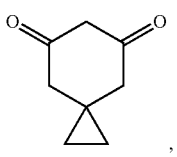

said method comprising cyclizing [1-(2-oxo-propyl)-cyclopropyl]-acetic acid methyl ester having the formula

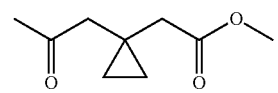

to form spiro[2.5]octane-5,7-dione, such as e.g. under conditions substantially as described herein by way of example in the following example, e.g. under Claisen condensation conditions in the presence of a suitable base (such as e.g. sodium methanolate) for enolisation, in a suitable solvent (such as e.g. tetrahydrofuran) at a suitable reaction temperature.

Further on, the present invention relates to spiro[2.5]octane-5,7-dione having the formula

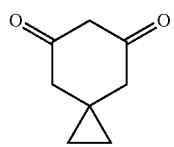

obtainable or obtained by cyclization of a [1-(2-oxo-propyl)-cyclopropyl]-acetic acid ester such as having the formula

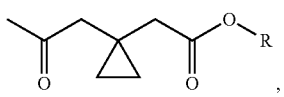

wherein R is $C_1$-$C_6$ alkyl, preferably $C_1$-$C_4$ alkyl (such as e.g. methyl, ethyl, propyl, isopropyl, or the like), more preferably $C_1$-$C_3$ alkyl or even more preferably $C_1$-$C_2$ alkyl, particularly methyl, such as e.g. substantially as described herein or analogously thereto.

Further on, the present invention relates to a method of preparing spiro[2.5]octane-5,7-dione having the formula

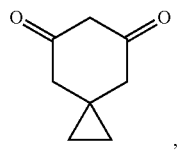

said method comprising cyclizing [1-(2-oxo-propyl)-cyclopropyl]-acetic acid ester having the formula

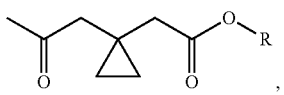

wherein R is $C_1$-$C_6$ alkyl, preferably $C_1$-$C_4$ alkyl (such as e.g. methyl, ethyl, propyl, isopropyl, or the like), more preferably $C_1$-$C_3$ alkyl or even more preferably $C_1$-$C_2$ alkyl, particularly methyl, to form spiro[2.5]octane-5,7-dione, such as e.g. under conditions substantially as described herein by way of example in the following example or analogously or similarly thereto, e.g. under Claisen condensation conditions in the presence of a suitable base (such as e.g. the respective metal alcoholate, particularly sodium methanolate) for enolisation, in a suitable solvent (such as e.g. tetrahydrofuran) at a suitable reaction temperature.

The intermediates and final compound of the invention may be obtained using methods of synthesis known in principle. Preferably, the intermediates involved and the final compound may be obtained by the following methods according to the invention which are described in more detailed example hereinafter.

The process steps may be performed substantially as described herein by way of example. A process or method of this invention may comprise one or more steps of converting and/or reacting the mentioned intermediates with the appropriate reaction partners, suitably under conditions as disclosed herein (e.g. by using the indicated reagents and/or solvents and/or temperatures, etc.).

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by gas chromatography (GC), High Pressure Liquid Chromatography (HPLC) or Thin Layer Chromatography, if desired.

EXAMPLES

In order that this invention be more fully understood, the following examples are set forth. These examples are for the purpose of illustrating preferred embodiments of this invention, and are not to be construed as limiting the scope of the invention in any way.

5  (1-Carboxymethyl-cyclopropyl)-acetic acid

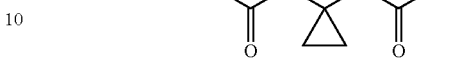

300 g of (1-cyanomethyl-cyclopropyl)-acetonitrile (2.5 mole) are combined with 3495 g of a 20% aqueous potassium hydroxide solution (12.5 mole, 5 eq) and the mixture is slowly heated to reflux. After 7.5 hours at reflux the mixture is cooled to room temperature and washed with 600 ml methyl tert-butyl ether. The aqueous phase is acidified to pH 2.5, and extracted two times with a total volume of 1500 ml of 2-methyltetrahydrofuran. The combined organic phases are washed with brine (110 ml), filtered and evaporated to dryness to yield a colorless solid.

Yield: 354.4 g (90% of theory; 83% assay-corrected)
Purity (HPLC a/a): 92%
1H NMR (400 MHz, D2O): δH=2.29 (s, 4H), 0.43 (s, 4H) ppm.

6-Oxa-spiro[2.5]octane-5,7-dione

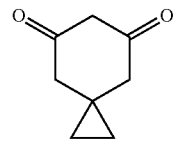

350 g crude (1-carboxymethyl-cyclopropyl)-acetic acid (2.2 mole, 92% purity, from step 1) are suspended in a mixture of 350 ml of mesitylene and 678 g of acetic anhydride (6.6 mole, 3 eq) and heated to 100° C. Upon reaching that temperature, the pressure is reduced to approximately 200 mbar and 45% of the solvent mixture are distilled off (distillation takes approx. 1 h). Then the mixture is slowly cooled to 0-5° C. and the precipitate is collected by filtration. The filter cake is washed with 87 ml of cold mesitylene and then dried in vaccuo at 40° C.

Yield: 252.1 g (81% of theory)
Purity (GC a/a): 99%
Mass spectrometry (EI+): m/z=140 [M]+
1H NMR (400 MHz, CDCl3): δH=2.61 (s, 4H), 0.63 (s, 4H) ppm.

Additional material can be obtained by concentrating the mother liquor to dryness and recrystallizing the residue from 3.5 vol of mesitylene (increasing the yield to 87%).

(1-Methoxycarbonylmethyl-cyclopropyl)-acetic acid

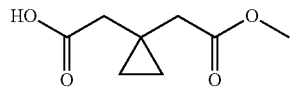

To a suspension of 150 g 6-oxa-spiro[2.5]octane-5,7-dione (1.07 mole) in 150 ml toluene are added 69 g methanol (2.1 mole, 2 eq) and 75 mg 4-dimethylaminopyridine (0.06 mole-%). The mixture is heated under reflux (approx. 85° C.). After one hour the mixture is cooled to 40-50° C. and 150 ml of toluene are added. Then vacuum is applied and 180 g of distillate are removed from the reaction mixture. The remaining solution is directly used in the next step.

Purity (GC a/a, derivatization with N-methy-N-(trimethylsilyl)trifluoroacetamide): 98%

1H NMR (400 MHz, CDCl3): δH=11.44 (br s, 1H), 3.63 (s, 3H), 2.41 (s, 2H), 2.38 (s, 2H), 0.52 (s, 4H) ppm.

By the use of the appropriate alcohols other than methanol (such as e.g. ethanol), the corresponding non-methyl esters (e.g. the ethyl ester) may be obtained analogously or similarly to the procedure as described for the methyl ester.

(1-Chlorocarbonylmethyl-cyclopropyl)-acetic acid methyl ester

The crude (1-methoxycarbonylmethyl-cyclopropyl)-acetic acid solution from the previous step (containing approx. 184 g (1.07 mole) (1-methoxycarbonylmethyl-cyclopropyl)-acetic acid in 180 ml of toluene) is diluted with 120 ml of toluene. Ten drops of dimethylformamide are added, the mixture is heated to 40° C. and a solution of 159 g of thionyl chloride (1.34 mole, 1.25 eq) in 75 ml of toluene is added dropwise. Then the mixture is slowly heated to 70° C. and stirred over night. Then the solvent is removed by vacuum distillation and the residue is co-evaporated three times with 185 ml of toluene each, yielding a dark oil.

Yield: 207.2 g (crude product, 102% (over two steps) of theory)

Purity (GC a/a, derivatization with isopropanol): 97%

1H NMR (400 MHz, CDCl3): δH=3.64 (s, 3H), 3.01 (s, 2H), 2.34 (s, 2H), 0.56 (s, 4H) ppm.

[1-(2-Oxo-propyl)-cyclopropyl]-acetic acid methyl ester

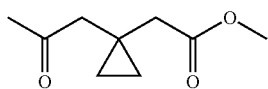

207.2 g crude (1-chlorocarbonylmethyl-cyclopropyl)-acetic acid methyl ester (approx. 1.07 mole, 97% purity, from step 4) are dissolved in 1428 ml of a 3:1 mixture of tetrahydrofuran and toluene. The mixture is cooled to −50° C. and 6.3 g of iron(III)bromide (0.02 mole, 0.02 eq) are added. Then 357 ml of methylmagnesium chloride in tetrahydrofuran (3 M solution in tetrahydrofuran, 1.07 mole, 1.0 eq) are added dropwise over two hours. After in-process control another 55 ml of methylmagnesium chloride in tetrahydrofuran (3 M solution in tetrahydrofuran, 0.17 mole, 0.15 eq) are added dropwise. Stirring is continued for 40 min, then the mixture is warmed to approx. 0° C., and diluted with 750 ml of methyl tert-butyl ether. Then the mixture is transferred onto a mixture of 27 ml of 37% hydrochloric acid and 480 ml of water. The phases are separated and the aqueous phase is extracted with 480 ml of methyl tert-butyl ether. The combined organic phases are washed twice with 480 ml of water (each) and then with 210 ml of brine, then dried over magnesium sulfate and evaporated to dryness to yield a dark red/brown oil.

Yield: 167.7 g (88% assay, 81% (over three steps) of theory)

Purity (GC): 92%

Mass spectrometry (EI+): m/z=170 [M]+, 155 [M-CH3]+

1H NMR (400 MHz, CDCl3): δH=3.66 (s, 3H), 2.53 (s, 2H), 2.36 (s, 2H), 2.13 (s, 3H), 0.57-0.54 (m, 2H), 0.48-0.45 (m, 2H) ppm.

Spiro[2.5]octane-5,7-dione

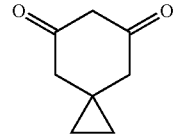

23.3 g of crude [1-(2-oxo-propyl)-cyclopropyl]-acetic acid methyl ester (60% purity, from step 5) are dissolved in 135 ml of tetrahydrofuran and 17.1 g of a sodium methanolate solution in methanol (30% in methanol) are added at room temperature and the mixture is stirred for six hours. Then the solution is diluted with 135 ml of methyl tert-butyl ether and quenched with 135 ml of water. Stirring is continued for five minutes, then the phases are separated. The aqueous phase is extracted with 67.5 ml of methyl tert-butyl ether, then acidified to pH 2-3 with 37% HCl and washed twice with 67.5 ml of methyl tert-butyl ether each. The combined organic phases are washed with 18 ml of water and concentrated to dryness. The crude product is stirred with 18 ml of cold methyl tert-butyl ether and then the precipitate is isolated by filtration. The filter cake is washed with 18 ml of cold methyl tert-butyl ether to yield the product as an off-white solid.

Yield: 6.6 g (60% of theory)

Purity (HPLC a/a): 99.8%

Mass spectrometry (EI+): m/z=138 [M]+

1H NMR (400 MHz, CDCl3): δH=3.45 (s, 2H), 2.43 (s, 4H), 0.54 (s, 4H) (keto form); 10.14 (br s, 1H), 5.54 (s, 1H), 2.25 (s, 4H), 0.47 (s, 4H) (enol form) ppm.

Alternative:

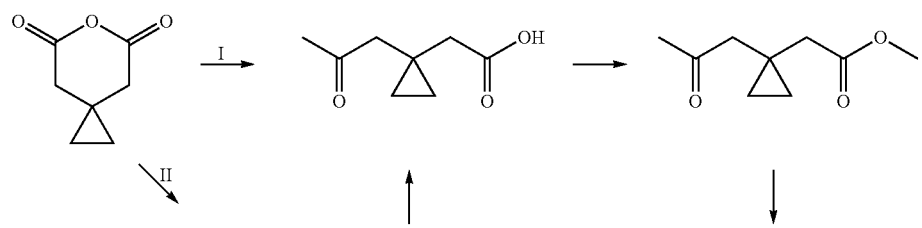

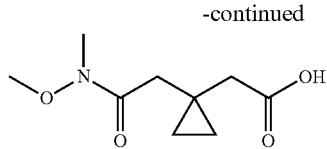

Alternative Route I

[1-(2-Oxo-propyl)-cyclopropyl]-acetic acid

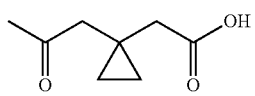

To a solution of 4.4 g 6-oxa-spiro[2.5]octane-5,7-dione (31 mmole) in 66 ml tetrahydrofuran are added 600 mg copper (I)chloride (6 mmole, 0.2 eq). The mixture is cooled to −20° C. and 9.8 ml of methylmagnesium bromide in 2-methyl tetrahydrofuran (3.2 M solution in 2-methyl tetrahydrofuran, 31 mmole, 1.0 eq) are added dropwise over 0.5 hours. The mixture is warmed to room temperature and stirred for 2 hours. 66 ml of water are added and the mixture is acidified to pH 3.0 by addition of 20.4 g of 2 M hydrochloric acid. 50 ml of methyl tert-butyl ether are added and the phases are separated. The aqueous phase is extracted again with 50 ml of methyl tert-butyl ether and the combined organic phases are washed with 20 ml of brine and concentrated to dryness. The resulting crude product is directly used in the next step (esterification to [1-(2-oxo-propyl)-cyclopropyl]-acetic acid methyl ester).

Yield: 4.9 g (crude)

[1-(2-Oxo-propyl)-cyclopropyl]-acetic acid methyl ester

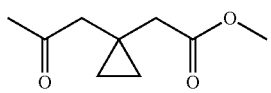

To a solution of 4.9 g crude [1-(2-oxo-propyl)-cyclopropyl]-acetic acid (31 mmole) in 73.5 ml methanol are added 1 ml of mesitylene (GC standard) and 2.5 ml of conc. hydrochloric acid. The mixture is heated to reflux for 1 hour and then concentrated to dryness. 40 ml of water are added to the residue and the resulting mixture is extracted with 100 ml of methyl tert-butyl ether in two portions. The combined organic phases are concentrated to dryness. The resulting crude product is directly used in the next step (spiro[2.5]octane-5,7-dione).

Yield: 5.3 g (crude)

Purity (GC a/a): 20.0%

By the use of the appropriate alcohols other than methanol (such as e.g. ethanol), the corresponding non-methyl esters (e.g. the ethyl ester) may be obtained analogously or similarly to the procedure as described for the methyl ester.

Spiro[2.5]octane-5,7-dione

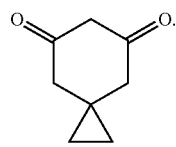

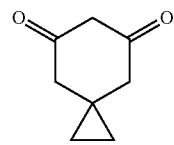

Experimental details: See above
Yield: 0.33 g (8% over three steps)
Purity (GC a/a): 99.7%
Alternative Route II:

{1-[(Methoxy-methyl-carbamoyl)-methyl]-cyclopropyl}-acetic acid

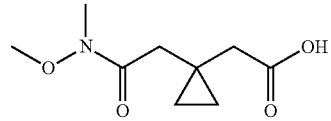

To a mixture of 5 g 6-oxa-spiro[2.5]octane-5,7-dione (36 mmole), 3.8 g of N,O-dimethylhydroxylamine hydrochloride (39 mmole, 1.1 eq) and 75 ml of dichloromethane are added 7 ml of pyridine (78 mmole, 2.2 eq) at 0-5° C. The solution is warmed to room temperature, stirred over night and washed with 50 ml of brine. The aqueous phase is extracted with 3×30 ml of dichloromethane and the combined organic phases are dried over magnesium sulfate and evaporated to dryness. The resulting crude product is directly used in the next step ([1-(2-oxo-propyl)-cyclopropyl]-acetic acid).

Yield: 7.9 g (crude, 110% of theory)
Purity (HPLC a/a): >99.9%

[1-(2-Oxo-propyl)-cyclopropyl]-acetic acid

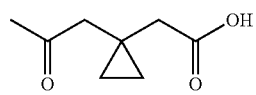

To a solution of 3.6 g crude {1-[(methoxy-methyl-carbamoyl)-methyl]-cyclopropyl}-acetic acid (18 mmole) in 54 ml of THF are added 24.5 ml of methyllithium (1.6 M solution in diethyl ether, 39.2 mmole, 2.2 eq) at <−75° C. Stirring is continued for 2 hours, then the mixture is quenched by addition of 2 ml of methanol and warmed to room temperature. 54 ml of water are added and the phases are separated. The aqueous product phase is washed with 27 ml of methyl tert-butyl ether, acidified to pH 2.5 by addition of conc. HCl and extracted three times with 27 ml ethyl acetate each. The combined organic phases are concentrated to dryness and the residue is directly used in the next step (esterification to [1-(2-oxo-propyl)-cyclopropyl]-acetic acid methyl ester).

[1-(2-Oxo-propyl)-cyclopropyl]-acetic acid methyl ester

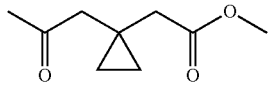

Experimental details: See above
Yield: 2.4 g (84% assay, 66% over three steps (assay-corrected))
Purity (GC a/a): 86.3%

The invention claimed is:
1. A method of preparing spiro[2.5]octane-5,7-dione having the formula

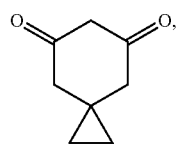

said method comprising cyclizing a [1-(2-oxo-propyl)-cyclopropyl]-acetic acid ester, having the formula

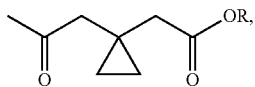

wherein R is $C_1$-$C_6$ alkyl, by subjecting the [1-(2-oxo-propyl)-cyclopropyl]-acetic acid ester to condensation conditions using a suitable base in a suitable solvent at a suitable reaction temperature for cyclization to form spiro[2.5]octane-5,7-dione.

2. The method of claim 1, wherein R is $C_1$-$C_3$ alkyl, the suitable base is a sodium alcoholate and the suitable solvent comprises tetrahydrofuran.

3. The method of claim 1, wherein R is methyl, the suitable base is sodium methanolate and the suitable solvent comprises tetrahydrofuran.

* * * * *